United States Patent [19]

Hauck et al.

[11] 4,173,640
[45] Nov. 6, 1979

[54] HYPOTENSIVE PERHYDRO NAPHTHALENE PENTOL DERIVATIVES

[75] Inventors: Frederic P. Hauck, Bridgewater; Michael E. Condon, Lawrenceville; Joyce Reid, Dayton, all of N.J.

[73] Assignee: E. R. Squibb & Sons, Inc., Princeton, N.J.

[21] Appl. No.: 821,891

[22] Filed: Aug. 4, 1977

[51] Int. Cl.² .................. A61K 31/445; C07D 211/34
[52] U.S. Cl. ............................ 424/267; 260/326.33; 260/326.5 C; 260/326.8; 260/343.3 R; 260/346.74; 260/348.54; 424/274; 546/206
[58] Field of Search .................. 260/293.56, 293.62, 260/326.33, 326.5 C; 424/267, 274; 546/206

[56] References Cited
U.S. PATENT DOCUMENTS

| | | | |
|---|---|---|---|
| 3,453,283 | 7/1969 | Lynch | 260/293.62 |
| 3,751,420 | 8/1973 | Hauck et al. | 260/326.33 |
| 3,894,031 | 7/1975 | Hauck et al. | 260/293.56 |
| 3,936,465 | 2/1976 | Hauck et al. | 260/293.56 |
| 4,022,791 | 5/1977 | Welch | 260/293.62 |
| 4,053,596 | 10/1977 | Hauck et al. | 260/239 BC |
| 4,092,318 | 5/1978 | Hauck et al. | 260/326.33 |

Primary Examiner—Alan L. Rotman
Assistant Examiner—Richard A. Schwartz
Attorney, Agent, or Firm—Lawrence S. Levinson; Burton Rodney

[57] ABSTRACT

Compounds are provided having the structure

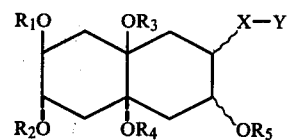

wherein $R_1$, $R_2$, $R_3$ or $R_4$ is hydrogen or acyl and $R_5$ is hydrogen or acyl, X is a straight or branched bivalent alkylene radical and Y is

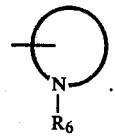

These compounds are useful in the treatment of hypertension.

13 Claims, No Drawings

HYPOTENSIVE PERHYDRO NAPHTHALENE PENTOL DERIVATIVES

COMPOUNDS OF THE INVENTION

The present invention relates to perhydro naphthalene derivatives which have a lowering effect on blood pressure and are useful in the treatment of hypertension, in mammalian species, for example, rats and dogs. In addition, the compounds of the invention can be employed as antibiotics. A compound of formula I (below) as well as its physiologically acceptable acid salts may be compounded according to pharmaceutical practice in oral or parenteral dosage forms, such as tablets, capsules, elixirs, injectables or powders for administration of about 100 mg to 400 mg per day, preferably 125 mg to 175 mg per day, in 2 to 4 divided doses.

Furthermore, the compounds of this invention are useful as water softeners.

The compounds of the invention have the general formula:

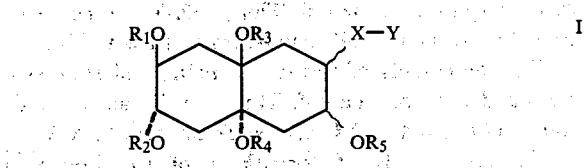

wherein $R_1$, $R_2$, $R_3$ and $R_4$ are hydrogen or acyl and $R_5$ is hydrogen or acyl, X is a single bond or a straight or branched chain bivalent alkylene radical, and Y is

wherein $R_6$ is hydrogen or lower alkyl.

X represents a single bond or a straight or branched chain bivalent aliphatic hydrocarbon group having from one to about ten carbon atoms in the normal chain, such as an alkylene group of the structure $(CH_2)_n$ wherein n is one or two, that is methylene or ethylene.

$R_1$, $R_2$, $R_3$, $R_4$ and/or $R_5$ may be an acyl radical of a hydrocarbon carboxylic acid of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and senecioic acids), the monocyclic aryl-carboxylic acids (e.g., benzoic and toluic acids), the monocyclic aryl-lower alkanoic acids [e.g., phenacetic, β-phenylpropionic, α-phenylbutyric, and 5-(p-methylphenyl)-pentanic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexene)pentenoic acid], and the like.

The alkanoic acids may include halogen substituents, for example, trifluoroacetic acid. In addition, other aycl groups which can be employed are angeloyl, veratroyl, vanilloyl, erythro-2-hydroxy-2-methyl-3-acetoxybutyryl, (1)-2-methylbutyryl; (d)-2-hydroxy-2-methylbutyryl; (d)-threo-2,3-dihydroxy-2-methylbutyryl and (1)-erythro-2,3-dihydroxy-2-methylbutyryl.

The term "lower alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Alkyl radicals substituted for F, Br, Cl or I are encompassed by the term halo-lower alkyl. Trifluoromethyl is a preferred halo-lower alkyl radical.

The term "monocyclic aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl, and the like), trinitrophenyl (e.g., picryl).

The term "monocyclic aryoyl" includes any of the above aryl groups linked to a carbonyl group.

The term "monocyclic cycloalkyl" and "monocyclic cycloalkenyl" includes cyclic radicals containing from 3 to 6 ring members (e.g., cyclopropyl, cyclobutyl, cyclopentyl, cyclohexyl, cyclobutenyl and cyclohexenyl).

The

group represents a 5- or 6-membered nitrogen heterocyclic ring containing a nitrogen atom. The above nitrogen heterocyclic radical may include one lower alkyl substituent on a nitrogen atom.

Examples of specific heterocyclic radicals represented by

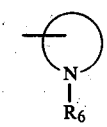

include the following

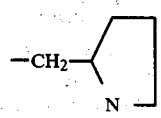 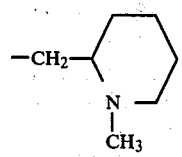

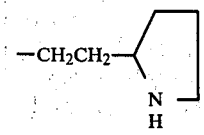 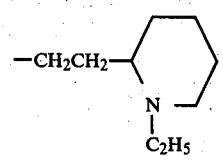

[Structures of various N-containing groups:]

−CH₂CH₂−(1-methylpyrrolidin-2-yl), −CH₂−(1-methylpiperidin-2-yl),

−CH₂−(1-methylpiperidin-4-yl), −CH₂−(4-methylpiperazin-1-yl via CH₂ to N−CH₃),

−CH₂−(pyrrolidin-2-yl, NH), −CH₂CH₂−(1-methylpyrrolidin-2-yl),

−CH₂−(piperidin-2-yl, NH), −CH₂−(1-ethylpyrrolidin-2-yl),

−CH₂CH₂−(1-propylpyrrolidin-2-yl)

The N-oxides of the compounds of formula I wherein Y represents a nitrogen containing heterocyclic radical can be formed by reacting such formula I compounds with a peracid such as m-chloroperoxy benzoic acid, perbenzoic acid or mono-perphthalic acid in a suitable solvent such as chloroform.

The compounds of formula I form acid addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is reacted with at least one equivalent of the desired alkylating agent.

Preferred are those compounds wherein X is a single bond, CH₂ or (CH₂)₂, Y is 2-piperidinyl or 2-pyrrolidinyl, with or without substituents, and $R_1$, $R_2$, $R_3$, $R_4$ and $R_5$ are hydrogen or acyl. Most preferred are those compounds wherein X is $CH_2$ or $(CH_2)_2$, Y is 1-methyl-2-piperidinyl or 1-methyl-3-pyrrolidinyl In all of the compounds of the invention, the $OR_1$, $OR_2$, $OR_3$ or $OR_4$ groups are axial and $OR_1$ and $OR_2$ are in trans configuration and $OR_3$ and $OR_4$ are in trans configuration.

The compounds of formula I include all stereoisomers and mixtures thereof. Thus, −X−Y can be cis or trans to $OR_3$ and −$OR_5$ can be cis or trans to X−Y.

The compounds of formula I include all stereoisomers and mixtures thereof. Thus −X−Y can be cis or trans to $OR_3$ and −$OR_5$ can be cis or trans to X−Y.

The compounds of formula I of the invention wherein X is $CH_2$ and Y is unsubstituted or substituted piperidinyl

[Structure of N-R⁶ substituted piperidinyl]

may be prepared by reacting an epoxide of the structure

[Structure II: 2,3-epoxy-1,2,3,4-tetrahydronaphthalene]    II with a lithium compound of the structure

[Structure: 2-(lithiomethyl)pyridine, Py−CH₂Li]

to form a compound of the structure

[Structure IV: tetrahydronaphthalenol with CH₂-pyridine substituent]    IV

The formula IV compound is reduced by reaction with hydrogen in the presence of a reduction catalyst such as platinum oxide and acetic acid to form a compound of the structure V

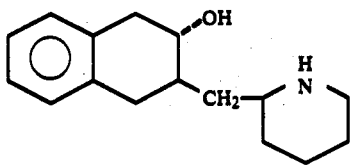     V

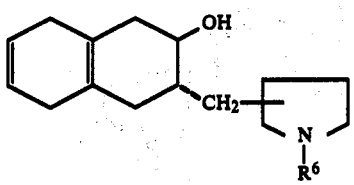     X which is then reacted with a mixture of formic acid and formaldehyde to yield a compound of structure VI, wherein $R^{6'}=CH_3$

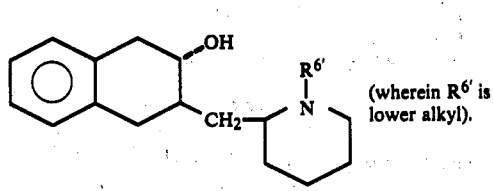  VI (wherein $R^{6'}$ is lower alkyl).

Alternatively, compound IV may be reacted with an alkyl halide and then reduced to form a compound of the structure VI.

The formula V or VI compound is then converted to the corresponding diene VII by reacting V or VI with a reducing metal, such as sodium or lithium in liquid ammonia in the presence of a proton source, such as a lower alcohol to form the corresponding diene

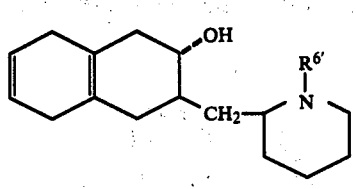   VII which is converted to the compounds of formula I of the invention as described hereinafter.

The compounds of the invention of formula I wherein X represents a methylene group and Y is substituted or unsubstituted pyrrolidinyl may be prepared by reacting an epoxide of formule II with a Grignard reagent of the structure

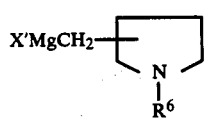   VIII wherein X' is Cl, Br or I. The compound so prepared, that is

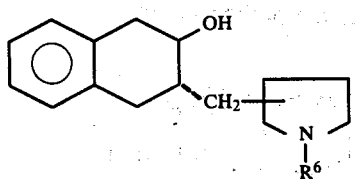   IX may be converted to the corresponding diene and thence to the compounds of formula I wherein X is methylene employing procedures described herein.

The compounds of the invention of formula I wherein X is a single bond and Y is substituted or unsubstituted pyrrolidinyl

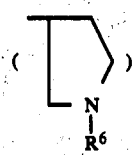

may be prepared by reacting 1,4-dihydronaphthalene with maleic anhydride

in accordance with the method of Alder Ann. 595 38 (1955) to form dihydro-3-(1,2-dihydro-2-naphthalenyl)-2,5-furandione of the structure

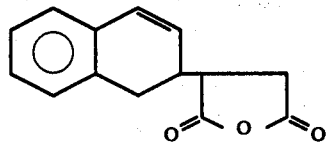   XI

The anhydride XI is reacted with an amine of the structure $R_6$—$NH_2$     XII to form a pyrrolidinedione compound of the structure

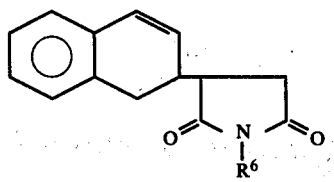   XIII which is then taken up in an inert solvent, such as dioxane, and added to a reducing agent, such as lithium aluminum hydride, in diethyl ether to form a compound of the structure

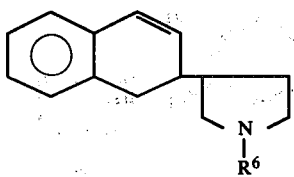
XIV

The compound of formula XIV is reacted with formic acid and an oxidizing agent, such as hydrogen peroxide to form a diol of the structure

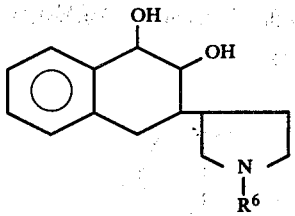
XV

The diol XV is then reacted with a reducing metal, such as sodium or lithium, in liquid ammonia in the presence of a proton source such as a lower alcohol to form diene XVI with concomitant loss of the benzylic alcohol group

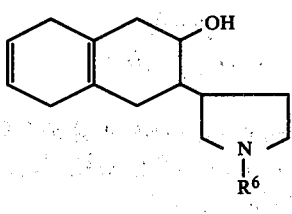
XVI

The above diene may be converted to the corresponding compounds of formula I wherein X is a single bond and Y is

employing procedures described herein.

Compounds of formula I wherein X is a single bond and Y is

may be prepared by reacting 2,3-epoxy-1,2,3,4-tetrahydronaphthalene

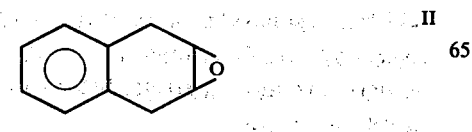
II with a 2-pyrrolyllithium compound of the structure

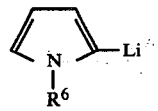
XVII in the presence of ethyl ether, to form a pyrrole compound of the structure

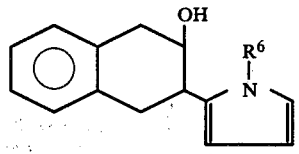
XVIII

The pyrrole compound of formula XVIII is dissolved, for example, in glacial acetic acid and hydrogenated over a catalyst, such as rhodium on aluminum to form a pyrrolidine of the structure

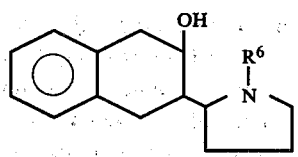
XIX

This compound is then reduced to the corresponding diene

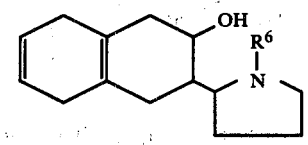
XX by reaction with a reducing metal, such as sodium or lithium, in liquid ammonia in the presence of a proton source, such as a lower alcohol, said diene being converted to compounds of formula I employing procedures as described herein.

The compounds of formula I wherein X is CH$_2$CH$_2$ and Y is

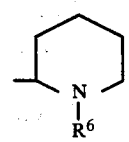

may be prepared by reacting a tetranaphthohydrofuranone compound of the structure

XXI with 2-pyridyl lithium

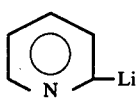

in ethyl ether to form the ketone XXIII

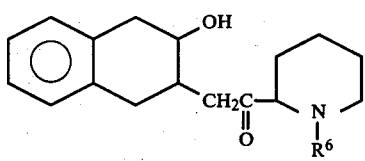

The ketone XXIII is quaternized with dimethyl sulfate, dissolved in an acid, such as acetic acid, and reduced by reaction with the mixed reducing agent, platinum dioxide plus palladium on carbon to form

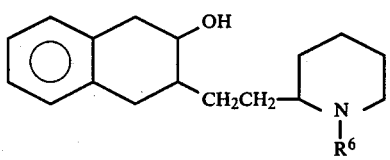

wherein $R^6$ is $CH_3$; amino alcohol XXIV is then converted to the corresponding diene by reaction with a reducing metal, such as sodium or lithium, in liquid ammonia in the presence of a proton source such as a lower alcohol to form the corresponding diene

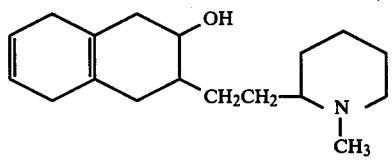

The above diene may be converted to the corresponding compounds of formula I wherein X is $CH_2CH_2$ and Y is

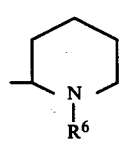

employing procedures as described herein.

Compounds of formula I wherein X is a single bond and Y is

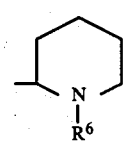

may be prepared as described above with respect to compounds of formula I wherein X is $CH_2CH_2$ and Y is

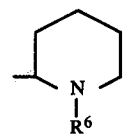

by substituting the 2,3-epoxy-1,2,3,4-tetrahydronaphthalene

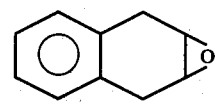

for the tetrahydronaphthofuran

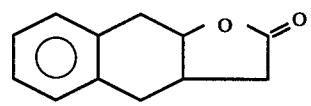

in the reaction with 2-pyridyl lithium.

Compounds of formula I wherein X is a single bond and Y is

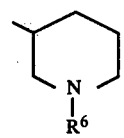

may be prepared by the method of Chem & Indus 357, May 1977, by reacting 2,3-epoxy-1,2,3,4-tetrahydronaphthalene with a solution of lithium diisopropylamide, hexamethylphosphoramide and a piperidone of the structure

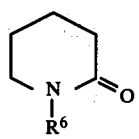

in tetrahydrofuran to form a compound of the structure

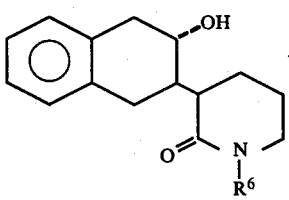

which is dissolved in an inert solvent such as dioxane and reduced with a reducing agent, such as lithium aluminum hydride in ethyl ether to form a compound of the structure

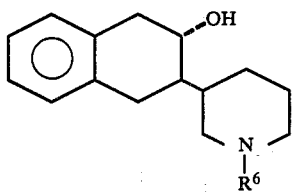

XXIX which may then be converted to the corresponding diene and thereafter converted to compounds of formula I in a manner as described herein.

The above procedure for making compounds of formula XXIX may be employed in preparing compounds of formula XXX

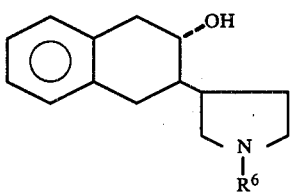

XXX by substituting pyrrolidone XXXI for piperidone XXVII

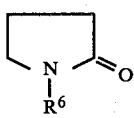

XXXI to form compounds of formula I wherein X is a single bond and Y is

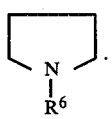

The pentol of formula I of the invention wherein $R_1$, $R_2$, $R_3$, and $R_4$ are hydrogen, can be formed by hydroxylating any of the aforementioned dienes to the corresponding pentol, for example, by reacting the diene with formic acid, and aqueous hydrogen peroxide, at temperatures ranging from about 20° to about 40° C. to form a mixture of esters, and then subjecting the mixture of esters to basic hydrolysis by dissolving the mixture of esters in a solvent boiling below about 100° C., such as a monohydric alcohol containing up to four carbon atoms (e.g., methyl alcohol, ethyl alcohol, propyl alcohol, isopropyl alcohol or butyl alcohol), and then treating the solution with a base, such as an alkali metal or alkaline earth metal hydroxide or alkoxide (e.g., sodium hydroxide, potassium hydroxide, barium hydroxide, calcium hydroxide, sodium methoxide or calcium diethoxide) and heating the mixture to temperatures ranging from about 40° to about 80° C., to form the pentol of the structure

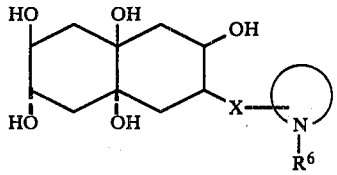

XXXII

In the above reaction the hydrogen peroxide is employed in a molar ratio to the diene of within the range of from about 2.2:1 to about 15:1 and preferably from about 2.2:1 to about 5:1. The base is employed in a molar ratio to the mixture of esters of within the range of from about 2.2:1 to about 10:1 and preferably from about 2.2:1 to about 5:1.

The pentol of Formula XXXII can be converted to the corresponding penta ester, i.e., where $R_1$, $R_2$, $R_3$, $R_4$ and $R_5$ are acyl as defined hereinbefore, by reacting the pentol with an acylating agent, such as a hydrocarbon carboxylic acid containing less than twelve carbon atoms as discussed hereinbefore, as the acid anhydride thereof, and an acid catalyst, such as perchloric acid, at a temperature within the range of from about −20° to about 0° C. Acid anhydride is employed in a molar ratio to the pentol of within the range of from about 5:1 to about 20:1 and preferably from about 5:1 to about 10:1 and the acid catalyst is employed in a molar ratio to the pentol of within the range of from about 1.1:1 to about 2:1 and preferably about 1.1:1 to about 1.5:1.

In an alternative procedure, the diene of formula XXXV can be converted to the corresponding pentol by dissolving the diene

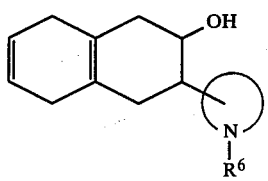

XXXIII in an organic carboxylic acid having up to about eight carbon atoms, such as acetic acid, treating the mixture with a silver salt corresponding to the acid, such as silver acetate (in a molar ratio of diene to silver salt of within the range of from about 1:2 to about 1:4 and preferably about 1:2) and iodine (in a molar ratio of diene to iodine of 1:1), heating the reaction mixture at a temperature of within the range of from about 60° to about 110° and preferably from about 80° to about 100°, to form a compound (depending on which acid and silver salt are employed) of the structure

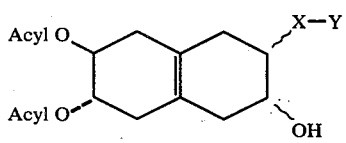

XXXIV

The above diester of the structure XXXIV can be converted to the corresponding triol by dissolving the diester in a suitable protonic solvent, such as ethyl alcohol, treating the solution with an excess of an aqueous base, such as aqueous sodium hydroxide or potassium hydroxide, to effect hydrolysis to the corresponding triol of the structure

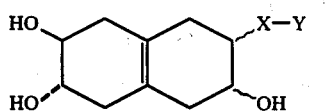   XXXV

The above triol can be converted to the pentol by reacting with formic acid and hydrogen peroxide (as described hereinbefore), at temperatures ranging from about 20° to about 40° C., preferably about 35°, and then treating the mixture (free of solvent) with an alcohol and a base (as described hereinbefore) to form the pentol wherein OR's (1 to 4) are axial and each pair of OR's (1 and 2, and 3 and 4) are trans.

The pentols or derivatives thereof can also be prepared by reacting the diene

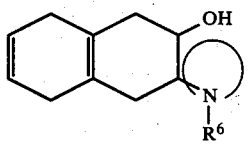   XXXIII with formic acid and one equivalent of aqueous hydrogen peroxide, and after removal of solvent, dissolving the residue in a alcohol-base as described hereinbefore to effect hydrolysis and form a triol olefin of the structure

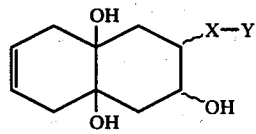   XXXVI

The above triol olefin can then be converted to the pentol as described hereinbefore with respect to the conversion of the triol olefin XXXV.

The pentol tetraacylate of formula I, wherein $R_5$ is H, can be prepared from the diene alcohol XXXIII by conversion to the succinate half ester

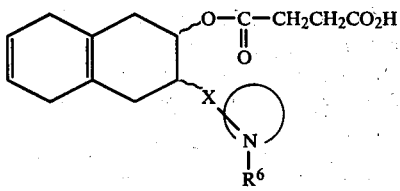   XXXVIII using succinic anhydride in pyridine, converting this to a salt with a strong non-participating acid, such as perchloric, in a carboxylic acid, such as acetic, oxidizing with the peracid of the same carboxylic acid, such as peracetic acid, in a ratio of peracid to diene of about 2:1 to about 3:1, precipitating the oxidation product by addition of non-polar diluents, such as benzene or ethyl ether, and acylating the crude oxidation product with the addition of the same carboxylic acid anhydride, such as acetic anhydride, to give, on dilution with ethyl ether, the tetra acyl succinate,

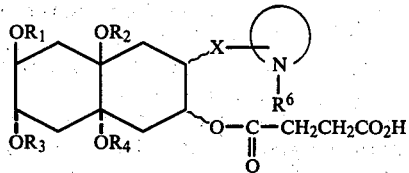   XXXIX

The tetraacyl succinate can be converted to the pentol tetra acylate by dissolving in an aqueous solution of

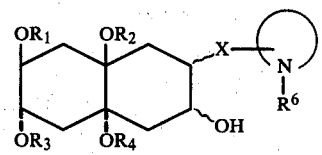   XL a weak base, such as sodium bicarbonate, and warming at temperatures from 40°–80° C. for a period of from 15 minutes to 1 hour.

The diene intermediates falling within the general structure

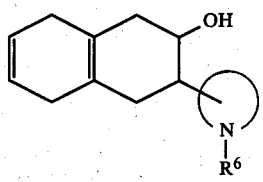   XXXIII are novel compounds.

The following Examples illustrate the present invention without, however, limiting the same thereto. All temperatures are expressed in degrees Centigrade.

EXAMPLE 1

2,3:4a,8a:6,7-trans-2,8a-cis-Decahydro-7-[(1-methyl-2-piperidinyl)methyl]-2,3,4a,6,8a-naphthalenepentol A. 1a,2,7,7a-Tetrahydronaphth[2,3-b]oxirane A solution of 1,4-dihydronaphthalene (32.5 g, 0.25 M) in 300 ml chloroform is cooled in an ice bath and, while stirring, is treated portionwise with 61 g (~20% excess) of 85% m-chloroperbenzoic acid. The mixture is stirred overnight at room temperature. After cooling in an ice bath, the solids are removed by filtration. The filtrate is washed twice with 5% $K_2CO_3$ solution, dried over $MgSO_4$, filtered and the solvent is removed in vacuo leaving 37.7 g of yellow partially crystalline material. This is distilled from a small amount of solid $K_2CO_3$. After removal of some low boiling material, 16.0 g (44%) of the desired epoxide is collected, boiling point 95°–110° at 0.1 mm.

B.

trans-1,2,3,4-Tetrahydro-3-(2-pyridinylmethyl)-2-naphthalenol

Phenyl lithium is prepared in ether (~400 ml) using 4.4 g (0.63 M) lithium and 47.2 g (0.3 M) bromobenzene. A solution of 31.4 g (0.31 M) of diisopropylamine in 75 ml ether is added dropwise and the mixture is stirred at room temperature a few minutes. A solution of 30.7 g (0.33 M) of α-picoline in 75 ml ether is then added dropwise and the orange-brown mixture is stirred a few minutes at room temperature. After cooling in an ice bath, a solution of 14.6 g (0.1 M) of the epoxide described above is added dropwise. The mixture is heated under reflux for 1 hour after warming to room temperature. While cooling in an ice bath, water is added dropwise. The layers are separated and the aqueous layer is reextracted with ether. The combined ether layers are dried over MgSO₄, filtered, and the solvent is removed in vacuo leaving 23.2 g (97%) of the title pyridyl compound.

C.
trans-1,2,3,4-Tetrahydro-3-(2-piperidinylmethyl)-2-naphthalenol

The pyridyl compound (23.2 g, 0.097 M) from Part B is dissolved in 150 ml of glacial acetic acid and treated with 2.0 g platinum oxide. This is hydrogenated at up to 52 psi. Uptake is complete in 4½ hours. The catalyst is removed by filtration through a Hy Flo pad. The solvent is removed in vacuo and the residue is dissolved in water, and basified with 50% NaOH solution. The product is extracted into chloroform, dried, and the solvent is removed in vacuo leaving 21.5 g of the title compound (90.5%).

D.
trans-1,2,3,4-Tetrahydro-3-[(1-methyl-2-piperidinyl)methyl]-2-naphthalenol trans-1,2,3,4-Tetrahydro-3-(2-piperidinylmethyl)-2-naphthalenol from Part D (21.5 g, 0.088 M) is dissolved in 20 ml 35% formaldehyde solution and 50 ml 98% formic acid. The mixture is heated overnight on a steam bath. The solution is taken to near dryness in vacuo. The residue is dissolved in water and basified with 50% NaOH solution. The material is extracted into chloroform, dried and the solvent is removed leaving a brown oil which shows a strong peak in the carbonyl region on the IR. This is dissolved in ethanol, NaOH solution is added and the mixture is heated for a few minutes on a steam bath. After diluting with ice water the mixture is extracted twice with ether. The ether extracts are dried and the solvent is removed leaving 23 g (quant) of the title compound.

E.
trans-1,2,3,4,5,8-Hexahydro-3-[(1-methyl-2-piperidinyl)methyl]-2-naphthalenol The crude N-methyl compound (0.088 M) is dissolved in ether (100 ml) and added to 1 liter liquid ammonia. Lithium ribbon (10 g) is added portionwise over a period of 10 minutes. After stirring a few minutes absolute ethanol is added dropwise until the color is discharged (150 ml added in 50 minutes). More ether is added and the ammonia is boiled off. While cooling in an ice bath, 1 liter water is added slowly. The layers are separated and the aqueous is reextracted with ether. The combined ether layers are dried over K₂CO₃, filtered, and the solvent is removed in vacuo leaving 20.0 g (87%) of viscous brown oil. IR, NMR, VPC consistent for desired product.

F.
2,3:4a,8a:6,7-trans-2,8a-cis-Decahydro-7-[(1-methyl-2-piperidinyl)methyl]-2,3,4a,6,8a-naphthalenepentol The crude diene from Part E (20.0 g, 0.0765 M) is added slowly to 100 ml cold 88% formic acid. Hydrogen peroxide (40 ml of 30%) is then added dropwise over a period of 45 minutes at temperature below 35°. After addition is complete, the temperature is allowed to rise to 45° and maintained at 35°-45° for 2 hours. The mixture is left stirring over the weekend in a large water bath at room temperature. The mixture is taken to near dryness in vacuo. Water is added once (neg. to starch-KI paper) and removed in vacuo. The residue is dissolved in 100 ml ethanol and, while cooling, is treated with a solution of 36 g KOH in 40 ml water. The mixture is heated on a steam bath for 30 minutes, and then is diluted to 300 ml with ice water. Four ether extractions give 7.4 g of very dark material. Three ethyl acetate extractions give an additional 11.8 g of material. The ethyl acetate extract is chromatographed on 250 g Activity IV basic alumina. The pentol (~83 g, 33%) is eluted with 2 to 5% methanol in CHCl₃. Crystallization of 2.4 g of this material from ethyl acetate-methanol gives 1.0 g of the title compound, m.p. 211°-221°.

EXAMPLE 2
2,6,8a-cis-Decahydro-7-[(1-methyl-2-piperidinyl)methyl]-2,3,4a,6,8a-naphthalenepentol, pentaacetate ester A chromatographed non-crystalline sample of 2,3:4a,8a:6,7-trans-2,8a-cis-decahydro-7-[(1-methyl-2-piperidinyl)methyl]-2,3,4a,6,8a-naphthalenepentol prepared as described in Example 1 (3.4 g, 0.0106 M) is dissolved in 40 ml acetic anhydride and 3 ml glacial acetic acid. The solution is cooled to −40° and 3.8 ml 70% perchloric acid is added dropwise over a period of 20 minutes. The mixture is stored overnight at −12°. After cooling to −30°, 20 ml methanol is added dropwise in 30 minutes. The mixture is then poured into 120 ml cold concentrated NH₄OH and the product is extracted into chloroform to give 5.2 g of white foam which crystallizes on addition of hexane. This material is chromatographed on Activity III neutral alumina, eluting the pentaacetate (3.55 g, 62%) with ethyl acetate. This is recrystallized from hexane-ethyl acetate to give the title compound, 2.4 g, shrinking 158°, melting 162°-165°.

EXAMPLE 3
trans-1,2,3,4-Tetrahydro-3-[(1-methyl-3-pyrrolidinyl)methyl]-2-naphthalenol

A.
trans-1,2,3,4-Tetrahydro-3-[(1-methyl-3-pyrrolidinyl)methyl]-2-naphthalenol A solution of 1.06 moles of 1-methyl-3-chloromethyl-pyrrolidine hydrochloride in 300 ml of water is saturated with solid potassium carbonate and extracted with hexane. The organics are dried over magnesium sulfate for 2 hours and evaporated to give 0.80 mole of the free base.

A mixture of 40 g (1.67 moles) of magnesium turnings and 200 ml of fresh THF under nitrogen is reacted with 3 ml of ethylene dibromide (1,2-dibromoethane). When the reaction has subsided, 150 ml of a solution of halide (0.80 mole) in 1 l. of THF is added. The mixture is then heated to a vigorous reflux and held there while the remaining halide is added over 1 hour. After an additional 15 minutes reflux, the reaction is allowed to cool to room temperature. Then a solution of 100 g (0.84 moles) of tetralin 2,3-epoxide in 500 ml of THF is added over one-half hour at a rate which maintains the mixture just under reflux. After the addition is complete the mixture is refluxed for 1 hour, cooled in an ice bath and treated with enough saturated ammonium chloride to get two layers. The aqueous layer is reextracted with THF and the organics evaporated without drying. The oily product is taken up in ether and extracted with 10% hydrochloric acid. The aqueous layer is basified with 10% sodium hydroxide and extracted twice with ether. The layers are separated and benzene is added to the ether to remove water azeotropically on evaporation. The resulting slurry is triturated with hexane to give about 95 g white solid adduct.

B.
trans-1,2,3,4,5,8-Hexahydro-3-[(1-methyl-3-pyrrolidinyl)methyl]-2-naphthalenol A suspension (0.1 mole) of the product from part A in 500 ml of liquid ammonia is treated with 60 ml of absolute ethanol, and then with 7 g (0.1 mole) of lithium over 25 minutes. After stirring 10 minutes longer, 30 ml of absolute ethanol is added to discharge the blue color. Ammonia is evaporated and enough water and ether added to dissolve all solids. The aqueous layer is reextracted with ether and the organics dried over potassium carbonate and evaporated. Hexane is added and evaporated to give about 20 g crude diene.

C.
2,3:4a,8a:6,7-trans-2,8a-cis-Decahydro-7-[(1-methyl-3-pyrrolidinyl)methyl]-2,3,4a,6,8a-naphthalenepentol The crude diene from Part B (20.0 g, 0.0765 mole) is added slowly to 100 ml cold 88% formic acid. Hydrogen peroxide (40 ml of 30%) is then added dropwise over a period of 45 minutes at temperature below 35°. After addition is complete, the temperature is allowed to rise to 45° and maintained at 35°-45° for 2 hours. The mixture is left stirring over the weekend in a large water bath at room temperature. The mixture is taken to near dryness in vacuo. Water is added once (neg. to starch-KI paper) and removed in vacuo. The residue is dissolved in 100 ml ethanol and, while cooling, is treated with a solution of 36 g KOH in 40 ml water. The mixture is heated on a steam bath for 30 minutes, and then is diluted to 300 ml with ice water and extracted with ether and ethyl acetate. The ethyl acetate extract is chromatographed on 250 g Activity IV basic alumina. The pentol is eluted with 2 to 5% methanol in CHCl$_3$. Crystallization of this material from ethyl acetate-methanol gives the title compound.

EXAMPLE 4
2,6,8a-cis-Decahydro-7-[(1-methyl-3-pyrrolidinyl)methyl]-2,3,4a,6,8a-naphthalenepentol, pentaacetate ester A chromatographed non-crystalline sample of 2,3:4a,8a:6,7-trans-2,8a-cis-decahydro-7-[(1-methyl-3-pyrrolidinyl)methyl]-2,3,4a,6,8a-naphthalenepentol prepared as described in Example 3 is dissolved in 40 ml acetic anhydride and 3 ml glacial acetic acid. The solution is cooled to −40° and 3.8 ml 70% perchloric acid is added dropwise over a period of 20 minutes. The mixture is stored overnight at −12°. After cooling to −20°, 20 ml methanol is added dropwise in 30 minutes. The mixture is then poured into 120 ml cold concentrated NH$_4$OH and the product is extracted into chloroform to give a white foam which crystallizes on addition of hexane. This material is chromatographed on Activity III neutral alumina, eluting the pentaacetate with ethyl acetate. This is recrystallized from hexane-ethyl acetate to give the title compound.

EXAMPLE 5
2,6,8a-cis-Decahydro-7-[(1-methyl-2-piperidinyl)methyl]-2,3,4a,6,8a-naphthalenepentol 2,3,4a,8a-tetraacetate ester A solution of 20 g of trans-1,2,3,4,5,8-hexahydro-3-[1-methyl-2-piperidinyl)methyl]-2-naphthalenol (as prepared in Example 1) in 200 ml of pyridine is treated with 10 g of succinic anhydride. After standing for 1 day at 25° C., the solvent is evaporated, toluene added and evaporated, to yield the succinate half ester. This is taken up in 140 ml of glacial acetic acid and 20 ml of acetic anhydride, cooled to 10° C. in ice, and treated carefully with 7 ml of 70% perchloric acid. After stirring 15 minutes, the addition of 35 ml of 40% peracetic acid is carried out over ¼ hour, at 15° C. The temperature is allowed to come to 25° C. for ¼ hour, then the bath temperature is raised to 45° C. for 1 hour. The mixture is then cooled to 5° C. and diluted with 400 ml of benzene. The upper phase is discarded, and the treatment repeated twice with benzene and twice using ethyl ether. The resulting viscous oil is cooled to −15° C. and dissolved cautiously in 70 ml of acetic anhydride. Another ½ ml of 70% perchloric is added, and after 1 day at −15° C., another 70 ml of acetic anhydride. After two more days at −15° C., the mixture is diluted with 2 l. of ethyl ether and the resulting dark gum dissolved in water and rendered basic with sodium bicarbonate. This solution is extracted quickly with ethyl acetate, then the aqueous is warmed at 60°-80° C. on a steam cone for 45 minutes. The resulting mixture is extracted with chloroform, dried using magnesium sulfate, and evaporated to 10 g of an oil.

Chromatography on neutral alumina, activity II, in ethyl acetate with increasing concentrations of methanol affords the desired product.

The above procedure may be employed to convert any of the dienes disclosed herein to the corresponding hydroxy tetraacetate.

EXAMPLE 6
3-(1,2,3,4,5,8-Hexahydro-3-hydroxy-2-naphthalenyl)-1-methyl-pyrrolidine

A.
3-(1,2-Dihydro-2-naphthalenyl)-1-methyl-2,5-pyrrolidinedione

Dihydro-3-(1,2-dihydro-2-naphthalenyl)-2,5-furandione is prepared by the method of Alder Ann. 595 38 (1955).

60 g of the above anhydride is added portionwise to a stirred 500 ml portion of aqueous methylamine. After addition is complete, the mixture is heated to boil off water and excess amine, ultimately to 210°-220° to complete the cyclization and form the title A compound.

B. 3-(1,2-Dihydro-2-naphthalenyl)-1-methylpyrrolidine

The 3-(1,2-dihydro-2-naphthalenyl)-1-methyl-2,5-pyrrolidinedione, 60 g, is taken up in dioxane and added dropwise to a suspension of 40 g of lithium aluminum anhydride (LAH) in 2 l. diethyl ether. After 5 hours at reflux, the mixture is decomposed with K$_2$CO$_3$ solution and filtered. Evaporation of the organic layer leaves 42.8 g of 3-(1,2-dihydro-2-naphthalenyl)-1-methylpyrrolidine which is distilled at 125°-150°/0.2 mm IR and NMR consistent, 28 g yield (54%).

C.
3-(3,4-Dihydroxy-1,2,3,4-tetrahydro-2-naphthalenyl)-1-methyl-pyrrolidine The above amine is dissolved in 300 ml cold formic acid and treated with an excess of 30% $H_2O_2$ added dropwise at 30° to 35° with cooling as required. After stirring overnight, the solution is evaporated on a rotary evaporator in vacuum to remove most of the formic acid. The residual liquid is dissolved in water and rendered strongly basic with NaOH solution. The 3-(3,4-dihydroxy-1,2,3,4-tetrahydro-2-naphthalenyl)-1-methyl pyrrolidine is extracted into $CH_2Cl_2$, dried and freed of solvent.

D.
3-(1,2,3,4,5,8-Hexahydro-3-hydroxy-2-naphthalenyl)-1-methyl-pyrrolidine The above diol is dissolved in a mixture of ether and $NH_3$ and treated portionwise with lithium metal cut in small pieces. After complete addition, absolute EtOH is added until the blue color is discharged. After the $NH_3$ has evaporated, the residue is cooled, diluted with water, and extracted with ether. Removal of solvents leaves 3-(1,2,3,4,5,8-hexahydro-3-hydroxy-2-naphthalenyl)-1-methyl-pyrrolidine as an oil.

EXAMPLE 7
Decahydro-7-(1-methylpyrrolidinyl)-2,3,4a,6,8a-naphthalenepentol Following the procedure of Example 3, but substituting the diene of Example 6, the title compound is obtained.

EXAMPLE 8
Decahydro-7-(1-methylpyrrolidinyl)-2,3,4a,6,8a-naphthalenepentol, pentaacetate ester ($2\beta,3\alpha,4a\alpha,6\beta,7\alpha,8a\beta$)

Following the procedure of Example 4, but substituting the naphthalenepentol of Example 7, the title compound is obtained.

EXAMPLE 9
2-[2-(1,2,3,4,5,8-Hexahydro-3-hydroxynaphthalenyl)ethyl]-1-methylpiperidine

A.
2,3,3a,4,9,9a-Hexahydro-2-oxonaphtho[2,3-b]-furan-3-carboxylic acid, ethyl ester Sodium ethoxide is prepared by adding 12.3 g (0.533 M) sodium portionwise to 600 ml absolute ethanol in a nitrogen atmosphere. After the sodium is gone, 85.5 g (0.533 M) of diethyl malonate is added dropwise over a period of 15 minutes during which time the mixture is heated to reflux. After 5 minutes a solution of 77.8 g (0.533 M) of 2,3-epoxy-1,2,3,4-tetrahydronaphthalene in 125 ml absolute ethanol is added dropwise over a period of 45 minutes at reflux. Before the addition is complete a large amount of solid precipitates making stirring difficult. After refluxing 5 hours the mixture is cooled and the pH is adjusted to 6 by adding glacial acetic acid. Most of the ethanol is removed in vacuo, water is added and the mixture is extracted 4 times with ether. The combined ether extracts are washed with saturated NaCl solution, dried, and freed of solvent in vacuo leaving an orange oil. Ether is added and white crystalline material is deposited. This is harvested and washed with ether to give 46.4 g (33.4%) of the title ester lactone.

B.
trans-3a,4,9,9a-Tetrahydronaphtho[2,3-b]furan-2-(3H)-one

A mixture of 35.9 g (138 mmol) of the ester lactone of Part A, 11.1 g (167 mmol) 85% KOH in 300 ml ethanol and 100 ml water is heated under reflux 45 minutes. After cooling most of the ethanol is removed in vacuo. Water is added and neutral material is removed by extracting once with ether. The aqueous layer is acidified with HCl and the acid lactone is extracted into ether. The combined ether extracts (3) are dried, filtered and most of the solvent is removed in vacuo.

The material is decarboxylated by heating in an oil bath. At ~190° the material becomes liquid and gas evolution is noted. The bath is held at 190°–210° until gas evolution ceases (~30 minutes). On cooling the material solidifies to give 23.7 g (91%).

C.
2-(3-Hydroxy-1,2,3,4-tetrahydronaphthalenyl)-ethyl-2-pyridyl ketone

A solution of 25 g of trans-3a,4,9,9a-tetrahydronaphtho[2,3-b]furan-2-(3H)-one in 250 ml ether is added to a solution of 2-pyridyl lithium (prepared from 2-bromopyridine and butyllithium) cooled to −20° C. After addition, the mixture is allowed to come to room temperature over several hours, then cooled again and treated with water. The separated, dried organics are taken to dryness and the product purified by chromatography on neutral alumina.

D.
2-[2-(3-Hydroxy-1,2,3,4-tetrahydronaphthalenyl)-ethyl]-1-methyl piperidine The 2-(3-hydroxy-1,2,3,4-tetrahydronaphthalenyl) ethyl 2-pyridyl ketone thus obtained is quaternized with dimethyl sulfate on the steam bath neat. After several hours, the salt is dissolved in HOAc and reduced over a mixture of $PtO_2$ and Pd/C to yield 2-[2-(3-hydroxy,1,2,3,4-tetrahydronaphthalenyl)ethyl]-1-methyl piperidine.

E.
2-[2-(1,2,3,4,5,8-Hexahydro-3-hydroxynaphthalenyl)ethyl]-1-methylpiperidine Following the procedure of Example 6, part D, but substituting the 2-[2-(3-hydroxy-1,2,3,4-tetrahydronaphthalenyl)ethyl]-1-methylpiperidine for the 3-(3,4-dihydroxy-1,2,3,4-tetrahydro-2-naphthalenyl)-1-methylpyrrolidine, the title E compound is obtained.

EXAMPLE 10
Decahydro-7-[2-(1-methylpiperidinyl)ethyl]-2,3,4a,6,8a-naphthalenepentol Following the procedure of Example 3, but substituting the diene of Example 9, the title compound is obtained.

EXAMPLE 11

Decahydro-7-[2-(1-methylpiperidinyl)ethyl]-2,3,4a,6,8a-naphthalenepentol, pentaacetate ester (2β,3α,4aα,6β,7α,8aβ)

Following the procedure of Example 4, but substituting the naphthalenepentol of Example 10, the title compound is obtained.

EXAMPLE 12

2-(1,2,3,4,5,8-Hexahydro-3-hydroxynaphthalenyl)-1-methyl piperidine

A.

2-(3-Hydroxy-1,2,3,4-tetrahydronaphthalenyl)-pyridine

A solution of 25 g of 2,3-epoxy-1,2,3,4-tetrahydronaphthalene in 250 ml ether is added to a solution of 2-pyridyl lithium (prepared from 2-bromopyridine and butyllithium) cooled to −20° C. After addition, the mixture is allowed to come to room temperature over several hours, then cooled again and treated with water. The separated, dried organics are taken to dryness, and the product purified by chromatography in neutral alumina.

B.

2-(3-Hydroxy-1,2,3,4-tetrahydronaphthalenyl)-1-methyl piperidine

The 2-(3-hydroxy-1,2,3,4-tetrahydronaphthalenyl)-pyridine thus obtained is quaternized with dimethyl sulfate on the steam bath neat. After several hours, the salt is dissolved in HOAc and reduced over a mixture of PtO$_2$ and Pd/C to yield 2-(3-hydroxy-1,2,3,4-tetrahydronaphthalenyl)-1-methyl piperidine.

C.

2-(1,2,3,4,5,8-Hexahydro-3-hydroxynaphthalenyl)-1-methylpiperidine

Following the procedure of Example 6, part D, but substituting the 2-(3-hydroxy-1,2,3,4-tetrahydronaphthalenyl)-1-methylpiperidine for the 3-(3,4-dihydroxy-1,2,3,4-tetrahydro-2-naphthalenyl)-1-methyl pyrrolidine, the title C compound is obtained.

EXAMPLE 13

Decahydro-7-(1-methylpiperidinyl)-2,3,4a,6,8a-naphthalenepentol

Following the procedure of Example 3, but substituting the diene of Example 12, the title compound is obtained.

EXAMPLE 14

Decahydro-7-(1-methylpiperidinyl)-2,3,4a,6,8a-naphthalenepentol, pentaacetate ester (2β,3α,4aα,6β,7α,8aβ)

Following the procedure of Example 4, but substituting the naphthalenepentol of Example 13, the title compound is obtained.

EXAMPLE 15

2-(1,2,3,4,5,8-Hexahydro-3-hydroxy-1,2,3,4-tetrahydronaphthalenyl)-1-methylpyrrolidine

A.

2-[2-(3-Hydroxy-1,2,3,4-tetrahydronaphthalenyl)]-1-methylpyrrole

To a solution of 1-methyl-2-pyrrolyllithium in ether prepared using 1-methylpyrrole, tetramethyl ethylenediamine and butyllithium [Acta Chem Second. 25 2596 (1971)] is added dropwise a solution of 35.5 g of 2,3-epoxy-1,2,3,4-tetrahydronaphthalene in 500 ml of ether at −10° C.−−20° C. After complete addition, the mixture is allowed to come to room temperature. After addition of water, the phases are separated, and the 2-[2-(3-hydroxy-1,2,3,4-tetrahydronaphthalenyl)]-1-methylpyrrole purified by chromatography on neutral alumina.

B.

2-[2-(3-Hydroxy-1,2,3,4-tetrahydronaphthalenyl)]-1-methylpyrrolidine

The purified pyrrole compound is dissolved in glacial acetic acid and hydrogenated over 5% rhodium on aluminum at 2–3 atm. of H$_2$ at ambient temperature until uptake is complete. After removal of catalyst, solvent is removed in vacuum and the residue dissolved in water and basified. The desired 2-[2-(3-hydroxy-1,2,3,4-tetrahydronaphthalenyl)]-1-methylpyrrolidine is extracted into CH$_2$Cl$_2$, dried and freed to solvent.

C.

2-(1,2,3,4,5,8-Hexahydro-3-hydroxynaphthalenyl)-1-methylpyrrolidine

Following the procedure of Example 6, part D, but substituting the 2-(3-hydroxy-1,2,3,4-tetrahydronaphthalenyl)-1-methylpyrrolidine for the 3-(3,4-dihydroxy-1,2,3,4-tetrahydro-2-naphthalenyl)-1-methylpyrrolidine, the title C compound is obtained.

EXAMPLE 16

Decahydro-7-(1-methylpyrrolidinyl)-2,3,4a,6,8a-naphthalenepentol

Following the procedure of Example 3, but substituting the diene of Example 15, the title compound is obtained.

EXAMPLE 17

Decahydro-7-(1-methylpyrrolidinyl)-2,3,4a,6,8a-naphthalenepentol, pentaacetate ester (2β,3α,4aα,6β,7α,8aβ)

Following the procedure of Example 4, but substituting the naphthalenepentol of Example 16, the title compound is obtained.

EXAMPLE 18

3-(3-Hydroxy-1,2,3,4-hexahydro-1,2,3,4-tetrahydronaphthalenyl)-1-methylpiperidine

A.

3-[2-(3-hydroxy-1,2,3,4-tetrahydronaphthalenyl)]-1-methylpiperidin-2-one (Method of Chem & Indus, 357, May 1977)

To a solution of 1.1 equivalents of lithium diisopropylamide in THF containing 1.7 equivalents of hexamethylphosphoramide at −80° is added a solution of 1-methyl 2-piperidone in THF. After 0.5 hour at that temperature, the solution is treated with a solution of 1 equivalent of 2,3-epoxy-1,2,3,4-tetrahydronaphthalene and allowed to come to room temperature over several hours. The mixture is treated with aqueous NH$_4$Cl and the layers separated. The dried organics are freed of solvent to leave crude product, 3-[2-(3-hydroxy-1,2,3,4-tetrahydronaphthalenyl)]-1-methylpiperidin-2-one.

B.

3-[2-(3-Hydroxy-1,2,3,4-tetrahydronaphthalenyl)]-1-methylpiperidine

The crude amide is dissolved in dioxane and added to a suspension of LAH in ether. After several hours at reflux, the mixture is decomposed with saturated $K_2CO_3$ solution, filtered and taken to dryness. The desired 3-[2-(3-hydroxy-1,2,3,4-tetrahydronaphthalenyl)]-1-methylpiperidine is freed of byproducts by chromatography on neutral alumina.

C.

3-(1,2,3,4,5,8-Hexahydro-3-hydroxynaphthalenyl)-1-methylpiperidine

Following the procedure of Example 6, part D, but substituting the 3-[2-(3-hydroxy-1,2,3,4-tetrahydronaphthalenyl)-]-1-methylpiperidine for the 3-(3,4-dihydroxy-1,2,3,4-tetrahydro-2-naphthalenyl)-1-methylpyrrolidine, the title C compound is obtained.

EXAMPLE 19

Decahydro-7-(1-methylpiperidine)-2,3,4a,6,8a-naphthalenepentol

Following the procedure of Example 3, but substituting the diene of Example 18, the title compound is obtained.

EXAMPLE 20

Decahydro-7-(1-methylpiperidine)-2,3,4a,6,8a-naphthalenepentol, pentaacetate ester ($2\beta,3\alpha,4a\alpha,6\beta,7\alpha,8a\beta$)

Following the procedure of Example 4, but substituting the naphthalenepentol of Example 19, the title compound is obtained.

EXAMPLES 21 to 26 trans-1,2,3,4-Tetrahydro-3-(2-pyridinylmethyl)-2-naphthalenol (prepared as described in Example 1, part B) is quaternized by reacting with an alkyl halide as shown in Column I of Table I set out below (following the procedure set out in Example 9, part D) to form the N-alkyl derivative set out in Column II. The N-alkyl derivative shown in Column II is then reduced and hydroxylated as described in Example 1, parts E and F, to form the product of the invention shown in Column III.

TABLE I

| Ex. No. | Column I<br>$R^6$—Br<br>$R^6$ | Column II<br>$R^6$ | Column III<br>$R^6$ |
|---|---|---|---|
| 21. | $C_2H_5$ | as in Column I | as in Column I |
| 22. | $C_3H_7$ | | |
| 23. | $C_4H_9$ | | |
| 24. | $C_5H_{11}$ | | |
| 25. | $C_6H_{13}$ | | |
| 26. | $C_7H_{15}$ | | |

EXAMPLES 27 to 32

Following the procedure of Example 2, but substituting the pentols of Examples 21 to 26, the pentaacetate esters of the Examples 21 to 26 pentols are obtained.

EXAMPLES 33 to 38

Following the procedure of Example 3, but substituting the magnesium compound shown in Column I of Table II below, the compound of the invention shown in Column II is obtained.

TABLE II

| Ex. No. | Column I<br>$R^6$ | Column II<br>$R^6$ |
|---|---|---|
| 33. | $C_2H_5$ | as in Column I |
| 34. | $C_3H_7$ | |
| 35. | $C_4H_9$ | |
| 36. | $C_5H_4$ | |
| 37. | $C_6H_{13}$ | |
| 38. | $C_7H_{15}$ | |

EXAMPLES 39 to 44

Following the procedure of Example 2, but substituting the pentols of Examples 33 to 38, the pentaacetate esters of the Examples 33 to 38 pentols are obtained.

EXAMPLES 45 to 50

Following the procedure of Example 6, but substituting the alkyl amine shown in Column I of Table III below, the diene shown in Column II is obtained. The diene may then be reduced and hydroxylated as described in Example 1, parts E and F, to form the product of the invention shown in Column III

TABLE III

| Ex. No. | Column I<br>$R^6NH_2$<br>$R^6$ | Column II<br>(tetrahydronaphthalenol with pyrrolidine)<br>$R^6$ | Column III<br>(pentol with pyrrolidine)<br>$R^6$ |
|---|---|---|---|
| 45. | $C_2H_5$ | as in Column I | as in Column I |
| 46. | $C_3H_7$ | | |
| 47. | $C_4H_9$ | | |
| 48. | $C_5H_{11}$ | | |
| 49. | $C_6H_{13}$ | | |
| 50. | $C_7H_{15}$ | | |

EXAMPLES 51 to 56

Following the procedure of Example 2, but substituting the pentols of Examples 45 to 50, the pentaacetate esters of the Examples 45 to 50 pentols are obtained.

EXAMPLES 57 to 62

2-(3-Hydroxy-1,2,3,4-tetrahydronaphthalenyl)methyl-2-pyridyl ketone (prepared as described in Example 9, part C), is quaternized by reacting with an alkyl halide as shown in Column I of Table IV set out below (following the procedure set out in Example 9, part D) to form the N-alkyl derivative set out in Column II. The N-alkyl derivative shown in Column II is then reduced and hydroxylated as described in Example 1, parts E and F, to form the product of the invention shown in Column III.

EXAMPLES 63 to 68

Following the procedure of Example 2, but substituting the pentols of Examples 57 to 62, the pentaacetate esters of the Examples 57 to 62 pentols are obtained.

EXAMPLES 69 to 74

2-(3-Hydroxy-1,2,3,4-tetrahydronaphthalenyl)-pyridine (prepared as described in Example 12, part A) is quaternized by reacting with an alkyl halide as shown in Column I of Table V set out below (following the procedure set out in Example 12, part B) to form the N-alkyl derivative set out in Column II. The N-alkyl derivative shown in Column II is then reduced and hydroxylated as described in Example 1, parts E and F, to form the product of the invention shown in Column III.

TABLE IV

| Ex. No. | Column I<br>$R^6-Br$<br>$R^6$ | Column II<br>(tetrahydronaphthalenol–CH$_2$CH$_2$–piperidine)<br>$R^6$ | Column III<br>(pentol–CH$_2$CH$_2$–piperidine)<br>$R^6$ |
|---|---|---|---|
| 57. | $C_2H_5$ | as in Column I | as in Column I |
| 58. | $C_3H_7$ | | |
| 59. | $C_4H_9$ | | |
| 60. | $C_5H_{11}$ | | |
| 61. | $C_6H_{13}$ | | |
| 62. | $C_7H_{15}$ | | |

TABLE V

| Ex. No. | Column I<br>$R^6-Br$<br>$R^6$ | Column II<br>(tetrahydronaphthalenol with piperidine)<br>$R^6$ | Column III<br>(pentol with piperidine)<br>$R^6$ |
|---|---|---|---|
| 69. | $C_2H_5$ | as in Column I | as in Column II |
| 70. | $C_3H_7$ | | |
| 71. | $C_4H_9$ | | |
| 72. | $C_5H_{11}$ | | |
| 73. | $C_6H_{13}$ | | |
| 74. | $C_7H_{15}$ | | |

EXAMPLES 75 TO 80

Following the procedure of Example 2, but substituting the pentols of Examples 75 to 80, the pentaacetate esters of the Examples 75 to 80 pentols are obtained.

EXAMPLES 81 TO 86

Following the procedure of Example 15, parts A and B, but substituting for 1-methyl-2-pyrrolyllithium the lithium compound shown in Column I of Table VI below, the N-alkyl pyrrolidine shown in Column II is obtained. The N-alkyl pyrrolidine shown in Column II is then reduced and hydroxylated as described in Example 1, parts E and F, to form the product of the invention shown in Column III.

EXAMPLES 99 TO 104

Following the procedure of Example 2, but substituting the pentols of Examples 93 to 98, the pentaacetate esters of the Examples 93 to 98 pentols are obtained.

What is claimed is:

1. A compound of the structure

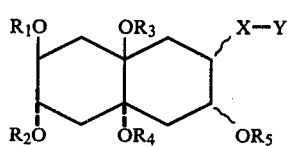

TABLE VI

| Ex. No. | Column I R⁶ | Column II R⁶ | Column III R⁶ |
|---|---|---|---|
| 81. | $C_2H_5$ | as in Column I | as in Column I |
| 82. | $C_3H_7$ | | |
| 83. | $C_4H_9$ | | |
| 84. | $C_5H_{11}$ | | |
| 85. | $C_6H_{13}$ | | |
| 86. | $C_7H_{15}$ | | |

EXAMPLES 87 TO 92

Following the procedure of Example 2, but substituting the pentols of Examples 81 to 86, the pentaacetate esters of the Examples 81 to 86 pentols are obtained.

EXAMPLES 93 TO 98

Following the procedure of Example 18, but substituting for the 1-methyl-2-piperidone starting material, the piperidone shown in Column I of Table VII set out below is used to form the N-alkyl derivative set out in Column II. The N-alkyl derivative shown in Column II is then reduced and hydroxylated as described in Example 1, parts E and F, to form the product of the invention shown in Column III.

wherein $R_1$, $R_2$, $R_3$, $R_4$ and $R_5$ are the same or different and are selected from the group consisting of hydrogen or an acyl radical of a hydrocarbon carboxylic acid of less than 12 carbons, an acyl radical of trifluoroacetic acid, angeloyl, veratroyl, vanilloyl, erythro-2-hydroxy-2-methyl-3-acetoxybutyryl, (1)-2-methylbutyryl, (d)-2-hydroxy-2-methylbutyryl, (d)-threo-2,3-dihydroxy-2-methylbutyryl and (1)-erythro-2,3-dihydroxy-2-methylbutyryl, X is a single bond or $CH_2$ or $CH_2CH_2$, Y is

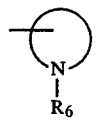

TABLE VII

| Ex. No. | Column I R⁶ | Column II R⁶ | Column III R⁶ |
|---|---|---|---|
| 93. | $C_2H_5$ | as in Column I | as in Column I |
| 94. | $C_3H_7$ | | |
| 95. | $C_4H_9$ | | |
| 96. | $C_5H_{11}$ | | |
| 97. | $C_6H_{13}$ | | |
| 98. | $C_7H_{15}$ | | | which represents a 5- or 6-membered saturated N-containing heterocyclic wherein $R^6$ is hydrogen or lower alkyl, or a stereoisomer thereof, or a physiologically acceptable acid salt thereof, or a physiologically acceptable quaternary salt thereof or an N-oxide thereof.

2. A compound according to claim 1 wherein $R_1$, $R_2$, $R_3$, and $R_4$ are hydrogen or alkanoyl of 1 to 3 carbons.

3. A compound according to claim 2 wherein $R_1$, $R_2$, $R_3$, $R_4$ and $R_5$ are alkanoyl of 1 to 3 carbons.

4. A compound according to claim 2 wherein $R_1$, $R_2$, $R_3$ and $R_4$ are acetyl.

5. A compound according to claim 2 wherein $R_1$, $R_2$, $R_3$, $R_4$ and $R_5$ are acetyl.

6. A compound according to claim 1 having the structure

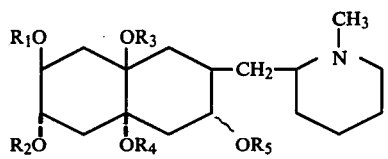

or a stereoisomer thereof.

7. The compound according to claim 6 wherein $R_1$, $R_2$, $R_3$, $R_4$ and $R_5$ are acetyl or a stereoisomer thereof.

8. The compound according to claim 6 wherein $R_1$, $R_2$, $R_3$, $R_4$ and $R_5$ are hydrogen.

9. The compound according to claim 1 wherein $R_1$, $R_2$, $R_3$, and $R_4$ are lower alkanoyl and $R_5$ is hydrogen.

10. A hypotensive composition comprising an effective hypotensive amount of a compound as defined in claim 1 and a pharmaceutically acceptable carrier therefor.

11. A method of treating hypertension in mammalian species, which comprises administering to a mammalian host an effective hypotensive amount of the composition as defined in claim 10.

12. A compound of the structure

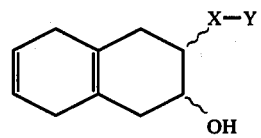

wherein X and Y are as defined in claim 1.

13. A compound of the structure

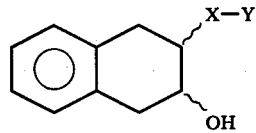

wherein X and Y are as defined in claim 1.

* * * * *

UNITED STATES PATENT AND TRADEMARK OFFICE
CERTIFICATE OF CORRECTION

PATENT NO. : 4,173,640
DATED : November 6, 1979
INVENTOR(S) : Frederic P. Hauck et al.

It is certified that error appears in the above-identified patent and that said Letters Patent are hereby corrected as shown below:

Column 4, fifth structure in the column, insert --III-- next to the structure.
Column 14, structure XXXIII should read -- 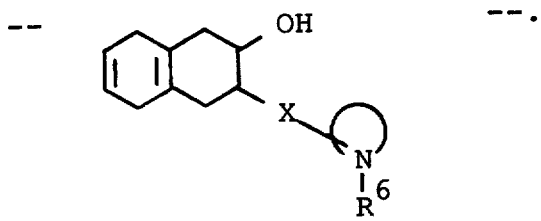 --.

Column 16, line 13, "83 g" should read --8.3 g--.
Column 17, line 60, "-20°" should read -- -30° --.

Signed and Sealed this

Twenty-fifth Day of March 1980

[SEAL]

Attest:

SIDNEY A. DIAMOND

Attesting Officer    Commissioner of Patents and Trademarks